(12) United States Patent
Forsyth et al.

(10) Patent No.: US 12,114,919 B2
(45) Date of Patent: Oct. 15, 2024

(54) MOVABLE ELECTRODES FOR CONTROLLED IRREVERSIBLE ELECTROPORATION ABLATIVE VOLUMES

(71) Applicant: Boston Scientific Scimed, Inc., Maple Grove, MN (US)

(72) Inventors: Bruce R. Forsyth, Hanover, MN (US); Larry D. Canady, Jr., Ham Lake, MN (US); Hong Cao, Maple Grove, MN (US); Timothy A. Ostroot, Cokato, MN (US); Jonathan Tyler Gorzycki, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 259 days.

(21) Appl. No.: 16/660,498

(22) Filed: Oct. 22, 2019

(65) Prior Publication Data
US 2020/0129230 A1  Apr. 30, 2020

Related U.S. Application Data

(60) Provisional application No. 62/749,898, filed on Oct. 24, 2018.

(51) Int. Cl.
*A61B 18/14* (2006.01)
*A61M 25/00* (2006.01)
*A61B 18/00* (2006.01)

(52) U.S. Cl.
CPC .......... *A61B 18/1492* (2013.01); *A61B 18/14* (2013.01); *A61M 25/0023* (2013.01);
(Continued)

(58) Field of Classification Search
CPC ........ A61B 18/1492; A61B 2018/0016; A61B 2018/00577; A61B 2018/00875;
(Continued)

(56) References Cited

U.S. PATENT DOCUMENTS 2,459,325 A  1/1949 Knowles
3,134,861 A  5/1964 Dempsey et al.
(Continued)

FOREIGN PATENT DOCUMENTS

JP  2009521993  6/2009
JP  2010259810  11/2010
(Continued)

OTHER PUBLICATIONS

"International Preliminary Report on Patentability," for PCT Application No. PCT/US2019/057596 mailed May 6, 2021 (9 pages).
(Continued)

*Primary Examiner* — Jaymi E Della
*Assistant Examiner* — Abigail M Ziegler
(74) *Attorney, Agent, or Firm* — Pauly, DeVries Smith & Deffner LLC

(57) ABSTRACT

A system for ablation is described herein including an inner electrode assembly with an inner elongate shaft and a distal electrode, an outer electrode assembly having an outer elongate shaft and a proximal electrode, wherein the outer electrode assembly defines a central passage configured to slidably receive the inner electrode assembly, wherein the distal electrode or the proximal electrode is axially moveable with respect to the other, and an energy source configured to be electrically connected to the distal electrode and the proximal electrode and configured to deliver a pulsed electric field (PEF). One of the distal electrode and proximal electrode is part of a first expandable electrode array comprising two or more electrode elements moveable between an unexpanded position and an expanded position.

19 Claims, 10 Drawing Sheets

(52) U.S. Cl.
CPC ............... *A61B 2018/0016* (2013.01); *A61B 2018/00196* (2013.01); *A61B 2018/00202* (2013.01); *A61B 2018/00577* (2013.01); *A61B 2018/00613* (2013.01); *A61B 2018/00875* (2013.01); *A61B 2018/143* (2013.01); *A61B 2018/1435* (2013.01); *A61B 2018/144* (2013.01); *A61B 2018/1467* (2013.01); *A61B 2018/1475* (2013.01); *A61M 2025/0024* (2013.01)

(58) Field of Classification Search
CPC .. A61B 2018/1475; A61B 2018/00196; A61B 2018/00613; A61B 2018/143; A61B 2018/144; A61B 2018/1467; A61M 2025/0024
See application file for complete search history.

(56) References Cited

U.S. PATENT DOCUMENTS

| | | | |
|---|---|---|---|
| 5,019,034 | A | 5/1991 | Weaver et al. |
| 5,672,173 | A | 9/1997 | Gough et al. |
| 5,697,927 | A | 12/1997 | Imran et al. |
| 5,718,246 | A | 2/1998 | Vona |
| 5,855,576 | A | 1/1999 | Leveen et al. |
| 6,010,613 | A | 1/2000 | Walters et al. |
| 6,043,066 | A | 3/2000 | Mangano et al. |
| 6,451,016 | B1 | 9/2002 | Karakozian |
| 7,229,438 | B2 * | 6/2007 | Young ................ A61B 18/148 606/41 |
| 7,291,146 | B2 | 11/2007 | Koenig et al. |
| 7,306,596 | B2 | 12/2007 | Hillier et al. |
| 7,416,549 | B2 | 8/2008 | Young et al. |
| 7,456,012 | B2 | 11/2008 | Ryttsén et al. |
| 7,517,346 | B2 | 4/2009 | Sloan et al. |
| 7,742,795 | B2 | 6/2010 | Stone et al. |
| 7,822,215 | B2 | 10/2010 | Carazo et al. |
| 7,918,852 | B2 | 4/2011 | Tullis et al. |
| 7,945,331 | B2 | 5/2011 | Vilims |
| 8,052,679 | B2 | 11/2011 | Young |
| 8,100,896 | B2 | 1/2012 | Podhajsky |
| 8,262,574 | B2 * | 9/2012 | Placek ................ A61B 18/1477 600/443 |
| 8,414,581 | B2 | 4/2013 | Shah et al. |
| 8,504,147 | B2 | 8/2013 | Deem et al. |
| 8,548,600 | B2 | 10/2013 | Deem et al. |
| 8,774,937 | B2 | 7/2014 | Mercanzini et al. |
| 8,788,042 | B2 | 7/2014 | Mercanzini et al. |
| 8,788,064 | B2 | 7/2014 | Mercanzini et al. |
| 8,882,764 | B2 | 11/2014 | Sutton et al. |
| 8,920,416 | B2 | 12/2014 | Pham et al. |
| 8,939,969 | B2 | 1/2015 | Temelli et al. |
| 8,989,859 | B2 | 3/2015 | Deem et al. |
| 9,002,460 | B2 | 4/2015 | Parker |
| 9,037,259 | B2 | 5/2015 | Mathur |
| 9,072,906 | B2 | 7/2015 | Mercanzini et al. |
| 9,125,667 | B2 | 9/2015 | Stone et al. |
| 9,149,329 | B2 | 10/2015 | Azamian et al. |
| 9,277,955 | B2 | 3/2016 | Herscher et al. |
| 9,955,946 | B2 | 5/2018 | Miller et al. |
| 10,022,182 | B2 | 7/2018 | Willard et al. |
| 10,039,596 | B2 | 8/2018 | Zarins et al. |
| 10,285,755 | B2 | 5/2019 | Stewart et al. |
| 2002/0042597 | A1 | 4/2002 | Hartlaub |
| 2003/0093007 | A1 | 5/2003 | Wood et al. |
| 2004/0047807 | A1 | 3/2004 | Meyer |
| 2006/0149226 | A1 | 7/2006 | Mccullagh et al. |
| 2007/0012507 | A1 | 1/2007 | Lyon |
| 2007/0016185 | A1 | 1/2007 | Tullis et al. |
| 2007/0203549 | A1 | 8/2007 | Demarais et al. |
| 2008/0188912 | A1 | 8/2008 | Stone et al. |
| 2008/0269739 | A1 * | 10/2008 | Young ................ A61B 18/1492 606/48 |
| 2010/0049192 | A1 * | 2/2010 | Holtz ................ A61N 1/36071 606/41 |
| 2010/0222677 | A1 | 9/2010 | Placek et al. |
| 2010/0298761 | A1 * | 11/2010 | Staal ................ A61N 1/327 604/20 |
| 2011/0077644 | A1 | 3/2011 | Pham et al. |
| 2011/0106221 | A1 | 5/2011 | Neal, II et al. |
| 2011/0160723 | A1 | 6/2011 | Tullis et al. |
| 2011/0238057 | A1 * | 9/2011 | Moss ................ A61B 18/1477 606/41 |
| 2012/0095461 | A1 | 4/2012 | Herscher et al. |
| 2012/0150172 | A1 | 6/2012 | Ortiz et al. |
| 2012/0220995 | A1 | 8/2012 | Ostrovsky et al. |
| 2012/0220999 | A1 | 8/2012 | Long |
| 2013/0089229 | A1 | 4/2013 | Kristo et al. |
| 2013/0096549 | A1 | 4/2013 | Organ et al. |
| 2013/0165916 | A1 | 6/2013 | Mathur et al. |
| 2013/0296839 | A1 * | 11/2013 | Condie ............ A61B 18/1206 606/33 |
| 2014/0271717 | A1 | 9/2014 | Goshayeshgar et al. |
| 2014/0303617 | A1 | 10/2014 | Shimada |
| 2014/0336639 | A1 * | 11/2014 | Young ................ A61B 18/148 606/41 |
| 2015/0202220 | A1 | 7/2015 | Stein et al. |
| 2015/0270634 | A1 * | 9/2015 | Buesseler ............ H01R 13/02 606/41 |
| 2016/0113709 | A1 * | 4/2016 | Maor ................ A61B 18/1492 606/41 |
| 2017/0143409 | A1 | 5/2017 | Taylor et al. |
| 2018/0132922 | A1 * | 5/2018 | Neal, II ............ A61B 18/1477 |
| 2020/0022649 | A1 * | 1/2020 | Rodriguez ......... A61B 18/1492 |
| 2021/0220038 | A1 * | 7/2021 | Kenneth ............ A61B 18/1402 |

FOREIGN PATENT DOCUMENTS

| | | |
|---|---|---|
| WO | 2004080384 | 9/2004 |
| WO | 2007078997 | 7/2007 |
| WO | 2013169741 | 11/2013 |
| WO | 2014130031 | 8/2014 |
| WO | 2020086677 | 4/2020 |

OTHER PUBLICATIONS

"Advancing Ablation Boundaries," RFA Medical Technology and Product Information accessed from website URL <www.rfamedical.com> on Sep. 10, 2019 (2018) 4 pages.

Akassoglou, Katerina et al., "Fibrin Inhibits Peripheral Nerve Remyelination by Regulating Schann Cell Differentiation," Neuron, vol. 33, 861-875, Mar. 14, 2002 (15 pages).

Atwal, Jasvinder K. et al., "PriB is a Functional Receptor for Myelin Inhibitors of Axonal Regeneration," Science, vol. 322, Nov. 7, 2008 (5 pages).

Bower, Matthew et al., "Irreversible Electroporation of the Pancreas: Definitive Local Therapy Without Systemic Effects," Journal of Surgical Oncology 2011; 9999:1-7 (7 pages).

Boyd, J.G. et al., "A dose-dependent facilitation and inhibition of peripheral nerve regeneration by brain-derived neurotrophic factor," European Journal of Neuroscience, vol. 15, pp. 613-626, 2002 (14 pages).

Bruners, Philipp et al., "A Newly Developed Perfused Unbrella Eletrode for Radiofrequency Ablation: An Ex Vivo Evaluation Study in Bovine Liver," Cardiovasc Intervent Radiol (2007) 30:992-998 (7 pages).

Christie, Kimberly J. et al., "PTEN Inhibition to Facilitate Intrinsic Regenerative Outgrowth of Adult Peripheral Axons," The Journal of Neuroscience, Jul. 7, 2010, 30(27):9306-9315 (10 pages).

Davies, Stephen et al., "Regeneration of Adult Axons in White Matter Tracts of the Central Nervous System," Nature. Dec. 18-25, 1997;390(6661):680-3 (4 pages).

"Delivering Energy Innovation: The New Cool-tip FR Ablation System E Series," Covidien Product Brochure, Feb. 2014 (4 pages).

Deodhar, Ajita et al., "Irreversible Electroporation Near the Heart: Ventricular Arrhythmias Can Be Prevented With ECG Synchronization," Vascular and Interventional Radiology:196, Mar. 2011 (6 pages).

(56) References Cited

OTHER PUBLICATIONS

Derry, W. B. et al., "Substoichiometric Binding of Taxol Suppresses Microtubule Dynamics," Biochemistry, 1995, 34 (7), pp. 2203-2211 (9 pages).
"Disposable RF Injection Electrodes," Cosman Medical, Inc., https://www.cosmanmedical.com/wp-content/uploads/2014/03/COSMANDisposable-Injection-RF-Electrodes-and-Needles-CR-CP-CN.pdf, Mar. 2014 (2 pages).
El Bejjani, Rachid et al., "Notch Signaling Inhibits Axon Regeneration," Neuron. Jan. 26, 2012; 73(2):268-278 (20 pages).
Ferrannini, Ele "The Target of Metformin in Type 2 Diabetes," The New England Journal of Medicine 371:Oct. 16, 2014 (2 pages).
"File History," for U.S. Appl. No. 15/357,795 downloaded Oct. 25, 2019 (592 pages).
Fournier, Alyson E. et al., "Identification of a receptor mediating Nogo-66 inhibition of axonal regeneration," Nature, vol. 409, Jan. 18, 2001 (6 pages).
"G4 RF Generator," https://www.bostonscientific.com/en-US/products/nerve-radio-frequency-ablation/g4-rf-generator.html available at least as early as Aug. 28, 2018., 4 pages.
Garcia-Perez, Luis-Emilio et al., "Adherence to Therapies in Patients with Type 2 Diabetes," Diabetes Therapy (2013) 4:175-194 (20 pages).
Greene, Lloyd A. et al., "Purine Analogs Inhibit Nerve Growth Factor-Promoted Neurite Outgrowth by Sympathetic and Sensory Neurons," J Neurosci. May 1990;10(5):1479-85 (7 pages).
"Haylard Coolief Sinergy Cooled Radiofrequency Kit," Instructions for Use, Haylard Sales, LLC, https://www.halyardhealth.com/media/265133/IFU-COOLIEF-SINERGY-Cooled-Radiofrequency-RF-Kit.pdf, Apr. 3, 2015 (84 pages).
"Haylard Health Radiofrequency Pain Management system," https://www.lao.halyardhealth.com/solutions/pain-management/chronic-pain-solutions/radiofrequency-products.aspx, known of at least as early as May 29, 2015., 5 pages.
Heller, Richard et al., "Electrically Mediated Delivery of Plasmid DNA to the Skin, Using a Multielectrode Array," Human Gene Therapy 21:357-362, Mar. 2010 (6 pages).
"International Search Report and Written Opinion," for PCT Application No. PCT/US2019/057596 mailed Feb. 4, 2020 (13 pages).
Ito, Nobutake et al., "Bipolar Radiofrequency Ablation: Development of a New Expandable Device," Cardiovasc Intervent Radiol (2014) 37:770-776 (7 pages).
Jessen, K.R. et al., "The repair Schwann cell and its function in regenerating nerves," J Physiol 594.13(2016) pp. 3521-3531 (11 pages).
Kapural, Leonardo et al., "Radiofrequency Ablation for Chronic Pain Control," Current Pain and Headache Reports 2001, 5:517-525 (9 pages).
"Leveen Needle Electrodes," Boston Scientific Corporation product information for Leveen Needle Electrode Family, Jul. 2015 (2 pages).
Levkovitz, Yechiel et al., "A Dominant Negative Egr Inhibitor Blocks Nerve Growth Factor-Induced Neurite Outgrowth by Suppressing c-Jun Activation: Role of an Egr/c-Jun Complex," The Journal of Neuroscience, May 15, 2002, 22(10):3845-3854 (10 pages).
Maclean, Charles D. et al., "Limitations of Diabetes Pharmacotherapy: results from the Vermont Diabetes Information System Study," BMC Family Practice 2006, 7:50 (6 pages).
Narayanan, G. et al., "Radiofrequency Ablation: Current Status," Boston Scientific Corporation Technique Spotlight, Jun. 2015 (8 pages).
"NeuroTherm Simplicity User Manual," Neuro Therm, http://www.cadaverworkshop.info/wp-content/uploads/2012/03/Simplicity-III-Manual.pdf, Mar. 2012 (13 pages).

"NT2000iX Radiofrequency Generator," https://www.neuromodulation.abbott/US/en/hcp/products/radiofrequency-chronic-pain/NT2000iX-radiofrequency-generator.html.html, known of at least as early as May 29, 2015., 3 pages.
"OsteoCool FR Ablation System," Treat Bone Tumors with Reproducible Precision, Medtronic Product Brochure 2019 (6 pages).
Park, Kevin K. et al., "Promoting Axon Regeneration in the Adult CNS by Modulation of the PTEN/mTOR Pathway," Science. Nov. 7, 2008;322(5903):963-966 (9 pages).
Pollo, Claudio et al., "Directional Deep Brain Stimulation: an Intraoperative Double-Blind Pilot Study," Brain Jul. 2014; 137(Pt 7):2015-26 (12 pages).
"Rf 3000 Generator," Boston Scientific Corporation Product Brochure, Jun. 2015 (6 pages).
Shen, Yingjie et al., "PTPσ Is a Receptor for Chondroitin Sulfate Proteoglycan, an Inhibitor of Neural Regeneration," Science. Oct. 2, 20093; 326(5952): 592-596 (5 pages).
Smith, Patrice D. et al., "SOCS3 deletion promotes optic nerve regeneration in vivo," Neuron. Dec. 10, 2009;64(5): 617-623 (15 pages).
"StarBurst XL Radiorequency Ablation Alectrodes," Angiodynamics Product Brochure, 2013 (2 pages).
Stichel, Christine C. et al., "The CNS Lesion Scar: New Vistas on an Old Regeneration Barrier," Cell Tissue Res. Oct. 1998;294(1):1-9 (9 pages).
"Stryker MultiGen 2 Radiofrequency Generator," https://www.stryker.com/us/en/interventional-spine/products/multigen2-rf-generator.html, known of at least as early as May 29, 2015., 2 pages.
"Stryker Venom Cannula and Electrode System," https://www.stryker.com/us/en/interventional-spine/products/venom-cannula-and-electrode-system.html, known of at least as early as May 29, 2015., 2 pages.
"Stryker Venom Cannula and Electrode System," Stryker Corporation, https://www.stryker.com/us/en/interventional-spine/products/venom-cannula-and-electrode-system.html, 2017 (3 pages).
"Surgical Technique," for OsteoCool FR Ablation System and Bone Access Kits, Medtronic Surgical Technique Guide 2019 (16 pages).
Szolcsanyi, Janos et al., "Resiniferatoxin: An Ultrapotent Selective Modulator of Capsaicin-Sensitive Primary Affert Neurons," J Pharmacol Exp Ther. Nov. 1990;255(2):923-8 (6 pages).
"The Vessix Renal Denervation System Background Information," Boston Scientific Corporation product factsheet Dec. 12, 2014 (3 pages).
"Vessix Renal Denervation System," Boston Scientific Corporation System Brochure, 2014 (3 pages).
Yang, Lynda et al., "Axon Regeneration Inhibitors," Neurol Res. Dec. 2008;30(10):1047-52 (6 pages).
Zhuo, Xiaohui et al., "Lifetim Direct Medical Costs of Treating Type 2 Diabetes and Diabetic Complications," Am. J. Prev. Med. 2013;45(3):253-261 (9 pages).
"Response to Communication Pursuant to Rules 161(1) and 162 EPC," for European Patent Application No. 19802430.9 filed Oct. 20, 2021 (8 pages).
"Office Action," for Japanese Patent Application No. 2021-522442 mailed May 17, 2022 (13 pages) with English Translation.
"Office Action," for Japanese Patent Application No. 2021-522442 mailed Jan. 10, 2023 (6 pages) No English Translation.
"Office Action," for Japanese Patent Application No. 2021-522442 mailed Jul. 25, 2023 (6 pages) with English Translation.
"First Office Action," for Chinese Patent Application No. 201980069879.6 mailed Dec. 6, 2023 (10 pages) No English translation.
"Communication Pursuant to Article 94(3) EPC," for European Patent Application No. 19802430.9 mailed May 27, 2024 (5 pages).

* cited by examiner

MOVABLE ELECTRODES FOR CONTROLLED IRREVERSIBLE ELECTROPORATION ABLATIVE VOLUMES

This application claims the benefit of U.S. Provisional Application No. 62/749,898 filed Oct. 24, 2018, the content of which is herein incorporated by reference in its entirety.

BACKGROUND

Pulsed Electric Field (PEF) ablation, including irreversible electroporation (IRE) is an ablation modality that applies either monophasic or biphasic high-voltage electrical pulses in approximately the microsecond range of 0.1 microseconds to 100 microseconds to deliver electrical field intensities that can affect the transmembrane potential of cells. The cells become permeabilized by the creation of surface aqueous nanopores, which can be induced to cause permanent alterations of the plasma lipid bilayer depending on the applied integrated field strength, which is controlled through the electric potential, the overall pulse width, the pulse frequency, and the number of pulses delivered. The difference between irreversible and reversible electroporation is the transition between temporary pores that can recover over the cell plasma membrane, or permanent nanopores that cannot be healed. Irreversible electroporation causes cell death both through necrosis and through an induction of a gradual cascade of apoptotic signals which eventually lead to cell death. Generally speaking, the PEF/IRE modality is non-thermal death mechanism and does not cause cell death through extensive thermal necrotic damage in its application, although there can be modest tissue heating and necrosis near the surface of the active electrodes. The significant benefit of IRE therapy is that the majority of tissue architecture, including collagen, arteries veins, ducts, nerves, and vasculature are mostly unaffected and resistant to the IRE treatment—these tissues maintain their structure without significant denaturation or permanent damage. This result is important for sensitive biological tissues that may be near vital organs, such as the pancreas, or critical vasculature that would otherwise be damaged by conventional thermal ablation techniques.

SUMMARY

One general aspect is a system for ablation including an inner electrode assembly and an outer electrode assembly. The inner electrode assembly includes an inner elongate shaft and a distal electrode. The outer electrode assembly includes an outer elongate shaft and a proximal electrode, where the outer electrode assembly defines a central passage configured to slidably receive the inner electrode assembly, where the distal electrode or the proximal electrode is axially moveable with respect to the other. The system also includes an energy source configured to be electrically connected to the distal electrode and the proximal electrode and configured to deliver a pulsed electric field (PEF). The system also includes where one of the distal electrode and proximal electrode is part of a first expandable electrode array including two or more electrode elements moveable between an unexpanded position and an expanded position.

Examples may include one or more of the following features. The system where the expanded position of the first expandable electrode array includes at least a first expanded position and a second, further expanded position, where the system is configured to deliver the PEF in the first expanded position and in the second expanded position. The system further including a sensing circuit connected to the distal electrode and the proximal electrode and configured to generate at least one signal corresponding to an impedance of tissue. The system where the distal electrode is part of the first expandable electrode array. The system where the proximal electrode is part of a second expandable electrode array including two or more electrode elements moveable between an unexpanded position and an expanded position. The system where the proximal electrode is part of the first expandable electrode array. The system where the system is configured to provide the distal electrode, the proximal electrode, and each of the two or more elements of the first expandable electrode array with an individually controlled electric polarity. The system further including an intermediate electrode assembly including an intermediate elongate shaft and an intermediate electrode, the intermediate elongate shaft defining a central passage configured to slidably receive the inner electrode assembly, where the intermediate elongate shaft is configured to be received within the central passage of outer electrode assembly. The system where the intermediate electrode is part of the first expandable electrode array. The system where the two or more electrode elements of the first expandable electrode array are two or more electrode tines movable by a linear force between the unexpanded position within a sheath and the expanded position. The system where the two or more electrode elements are movable by a rotationally-acting mechanism between the unexpanded position and the expanded position. The system where the two or more electrode elements are movable by a radial-acting mechanism between the unexpanded position and the expanded position. The system where the two or more electrode elements are movable by a linear force between the unexpanded position and the expanded position. The system where the expandable electrode array is an elongate electrode array configured to contact an elongated portion of a vessel wall. Implementations of the described techniques may include hardware, a method or process, or computer software on a computer-accessible medium.

One general aspect is a system for ablation including an inner electrode assembly and an outer electrode assembly. The inner electrode assembly includes an inner elongate shaft and a distal electrode array, the distal electrode array including two or more electrode tines moveable by a linear force between an unexpanded position within the inner electrode shaft and an expanded position. The outer electrode assembly includes an outer elongate shaft and a proximal electrode array, the proximal electrode array including two or more electrode tines moveable by a linear force between an unexpanded position within the outer elongate shaft and an expanded position, where the outer electrode assembly defines a central passage configured to slidably receive the inner electrode assembly, where the distal electrode array or the proximal electrode array is axially moveable with respect to the other. The system also includes an energy source configured to be electrically connected to the distal electrode array and the proximal electrode array and configured to deliver a pulsed electric field (PEF).

One general aspect includes an ablation method including providing an ablation probe including an inner electrode assembly and an outer electrode assembly, where the inner electrode assembly includes an inner elongate shaft and a distal electrode and the outer electrode assembly includes an outer elongate shaft and a proximal electrode, where the outer electrode assembly defines a central passage configured to slidably receive the inner electrode assembly. The ablation probe of this method also includes an expandable electrode array including two or more electrode elements, where the expandable electrode array includes either the distal electrode or the proximal electrode. The ablation method also includes inserting the ablation probe into tissue of a patient. The ablation method also includes moving the expandable electrode array from an unexpanded position to an expanded position. The ablation method also includes delivering a pulsed electric field (PEF) to the distal electrode and the proximal electrode. The ablation method also includes moving one of the distal electrode and the proximal electrode axially with respect to the other.

Examples may include one or more of the following features. The method where delivering the PEF occurs while moving one of the distal electrode and the proximal electrode axially with respect to the other. The method where the distal electrode is part of the expandable electrode array and where delivering the PEF occurs while moving the proximal electrode axially with respect to the distal electrode. The method further including delivering a second PEF after performing at least one of the following steps: moving the distal electrode and the proximal electrode axially with respect to each other; moving the proximal electrode axially with respect to the distal electrode while the proximal electrode is held stationary; moving the expandable electrode array from the expanded position to the unexpanded position, moving the expandable electrode array axially, and moving the expandable electrode array from the unexpanded position to the expanded position; and moving the expandable electrode array from a first expanded position to a second further expanded position. The method further including providing the distal electrode, the proximal electrode, and each of the two or more electrode elements of the expandable electrode array an individual electric polarity. Implementations of the described techniques may include hardware, a method or process, or computer software on a computer-accessible medium.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

DETAILED DESCRIPTION

Figure 1:
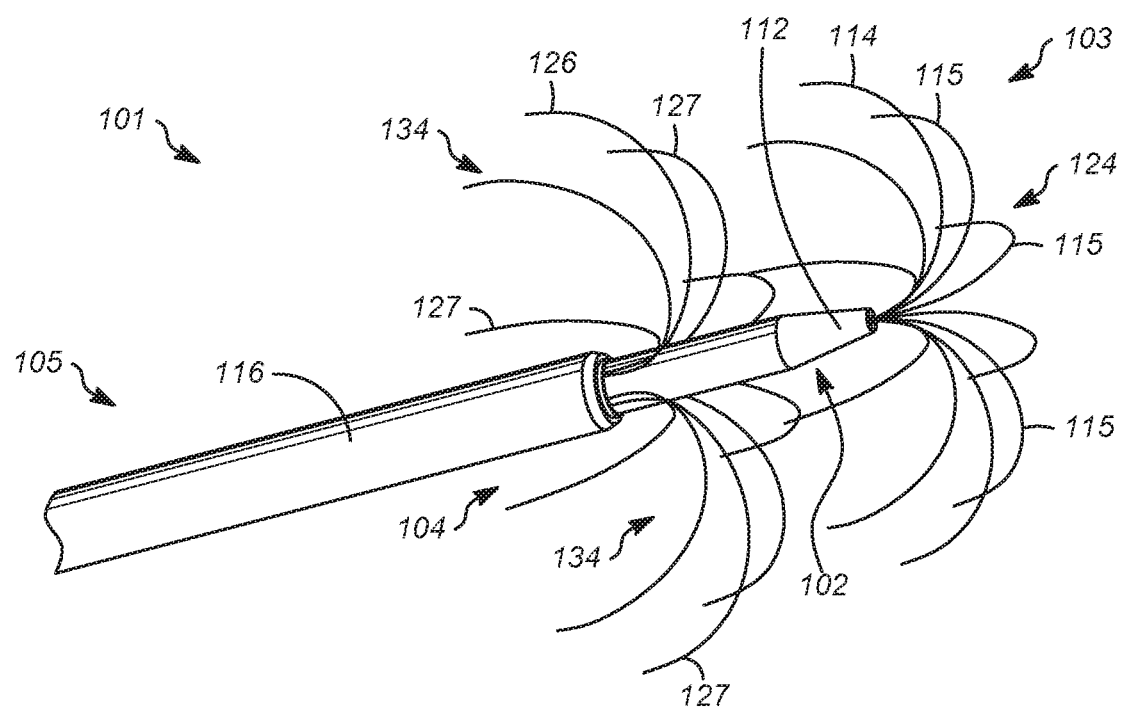
FIG. 1 is a perspective view of an ablation probe according to some examples.

The present disclosure provides ablation devices that use multiple movable electrodes to create ablation lesions of a controlled size and shape. In some examples, the ablation devices can be used to create cylindrical lesions as a first electrode is moved in relation to a second electrode. In some examples, ablation can be performed at fixed points for the moving electrode. In alternative examples, ablation can be performed continuously as one electrode is moved in relation to a second electrode. This allows a physician to ablate a precise treatment area.

In some examples, the ablation devices include one or more expandable electrode arrays. The expandable electrode arrays each contain multiple electrode elements. In some examples, the electrode elements can be curved tines that are retractable and expandable into and out of a lumen of the ablation device. In alternative examples, an expandable electrode array is expanded using a rotationally-acting mechanism. In alternative examples, an expandable electrode array includes an expandable balloon member. In alternative examples, an expandable electrode array is expanded using a linear force, such as using a push and pull wire to expand the electrode assembly.

In some examples, conductive bipolar or monopolar circuits can be constructed using either pre-shaped electrodes, wires, hoops, or other structures embedded into an expandable design. An external grounding pad is provided in monopolar device systems. In some examples, helical electrodes, spiral electrodes, wound circuits, and flexible circuits are attached to an expandable structure, including an expandable sheath or catheter. In some examples, the electrode elements can be deployed to cover an extended axial length along an elongated shaft of the ablation device. This enables the electrodes to reach a tissue wall inside a constricted lumen or other internal cavity or space through the application of radial force by the expandable electrode assembly.

Enabling individual electrodes, electrode arrays, or both to be controlled in size and location before and during activation of the electrodes allows a physician to affect the size, shape, and lesion depth during ablation.

In some examples, a control system selective switching or multiplexing of certain electrode pairs for axial or radial lesion size and shape control. Multiplexed, concurrent serial, or parallel switching electrodes allows for selective directional ablation with direct apposition of electrodes to a tissue surface. The application of a pulsed electric field can then provide controlled and precise bilateral or unilateral circumferential directional energy delivery, causing permeability of the cell membrane. Multidirectional electrode termination ends can provide discrete, highly electrically active electrodes using partial insulation for internal masking.

In various examples of systems for ablation, the system includes an inner electrode assembly comprising an inner elongate shaft and a distal electrode and an outer electrode assembly comprising an outer elongate shaft and a proximal electrode. The outer electrode assembly defines a central passage configured to slidably receive the inner electrode assembly. In other words, the central passage is configured to allow the inner electrode assembly to slide or move axially with respect to the outer electrode assembly. As a result, the distal electrode or the proximal electrode is axially moveable with respect to the other. The system further includes an energy source configured to be electrically connected to the distal electrode and the proximal electrode and configured to deliver a pulsed electric field (PEF). One of the distal electrode and proximal electrode is part of a first expandable electrode array comprising two or more electrode elements moveable between an unexpanded position and an expanded position.

Figure 2:
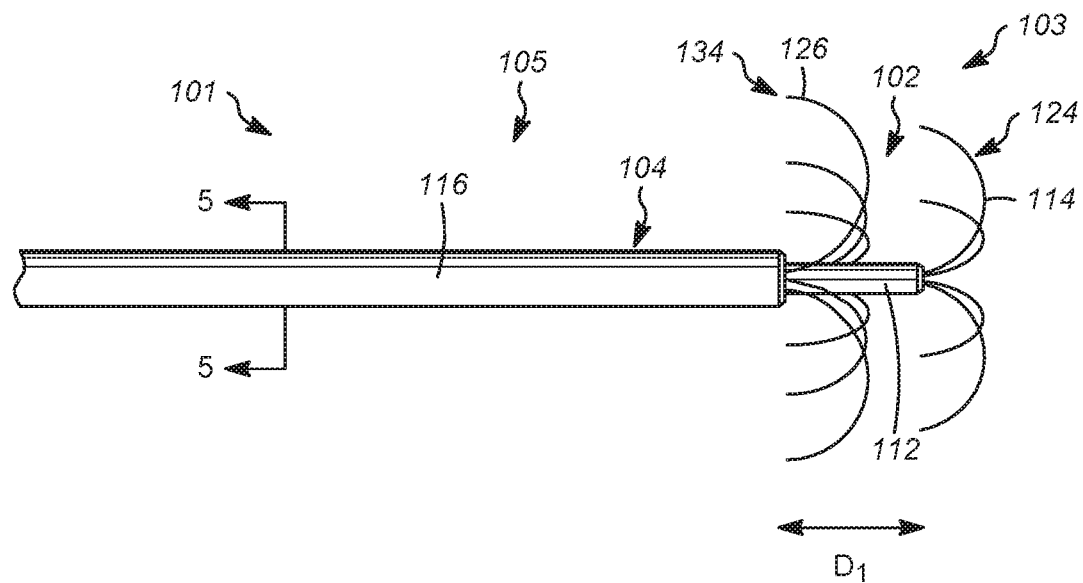
FIG. 2 is a side view of the ablation probe of FIG. 1 in a first configuration according to some examples.
Figure 3:
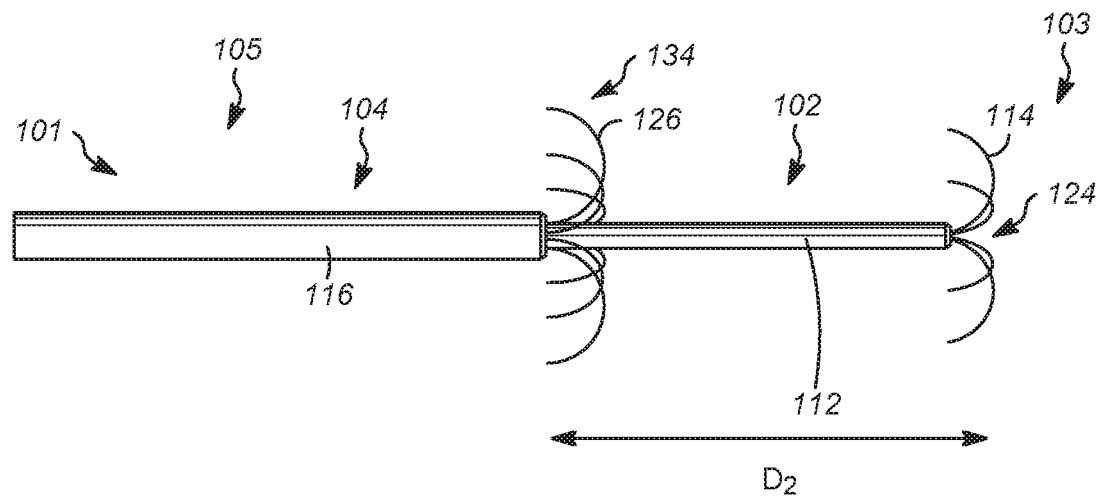
FIG. 3 is a side view of the ablation probe of FIG. 1 in a second configuration according to some examples.

Turning now to the drawings, FIG. 1 shows an ablation device according to some examples. FIGS. 1 and 2 show perspective and side views, respectively, of the ablation device in a first configuration, and FIG. 3 shows a side view of the ablation device in a second configuration. The ablation device 101 includes an inner electrode assembly 102 and an outer electrode assembly 104. The ablation device 101 is configured for pulsed electric field ablation, for example reversible or irreversible electroporation. The ablation device 101 includes a distal portion 103 and a proximal portion 105. As used herein, the words proximal and distal express a spatial relationship between two portions. A portion that is designated as being distal is positioned closer to the insertion end of the system than a portion that is designated as being proximal.

The inner electrode assembly 102 includes an inner elongate sheath or shaft 112 and a distal electrode 114. In some examples, the inner electrode assembly 102 has a plurality of distal electrodes 114. In some examples, the distal electrode 114 is part of the plurality of distal electrodes 114. In some examples, including that of FIG. 1, the inner electrode assembly 102 also comprises a distal expandable electrode array 124 with two or more electrode elements, including the distal electrode 114 and the plurality of distal tines 115. In the example of FIG. 1, the distal expandable electrode array 124 includes a plurality of electrodes that collectively form an umbrella shape. The plurality of electrode tines 115 is movable by a linear force between an unexpanded position retracted inside of the inner elongate shaft 112 and the expanded position seen in FIG. 1.

The outer electrode assembly 104 includes an outer elongate sheath or shaft 116. The outer electrode assembly 104 defines a central passage that allows the outer electrode assembly 104 to slidably receive the inner electrode assembly 102. The outer electrode assembly 104 further includes a proximal electrode 126. In some examples, the outer electrode assembly 104 includes a plurality of proximal electrodes 127. In some examples, the proximal electrode 126 is part of the plurality of proximal electrodes 127. In some examples, including that of FIG. 1, the outer electrode assembly 104 includes a proximal expandable electrode array 134 with two or more electrode elements, including the proximal electrode 126 and the plurality of proximal electrodes 127.

In some examples, the electrode tines 115 and the electrode tines 127 are made of a shape memory material, such as Nitinol. The tines can be retracted inside of a lumen, which causes the tines to straighten to fit the interior of the lumen. When the tines are deployed outside of the lumen, the tines resume a preset shape, such as a straight, angled, or curved shape.

The distal electrode 114 and the proximal electrode 126 are axially movable with respect to one another to control the size and shape of an ablation lesion. As used herein, axial motion refers to movement of an object in a direction corresponding to the axis of the device. Turning to FIGS. 2-3, the inner elongate shaft 112 and the outer elongate shaft 116 are axially movable with respect to each other. In the example of FIGS. 2-3, the inner elongate shaft 112 is disposed inside a lumen of the outer elongate shaft 116 and can move axially within the lumen with respect to the outer elongate shaft 116. The inner and outer elongate shaft 112, 116 are able to change their configuration such that the inner elongate shaft 112 can be made to protrude out of, or retract into, the outer elongate shaft 116. FIG. 2 demonstrates a first protruded configuration in which the inner elongate shaft 112 protrudes a first distance D1 from the outer elongate shaft 116.

FIG. 3 demonstrates a second protruded configuration in which the inner elongate shaft 112 protrudes a second distance D2 from the outer elongate shaft 116. By adjusting the protrusion distance of the inner shaft 112 relative to the outer shaft 116, the distance between the proximal and distal electrodes is also adjusted. For example, in the first protruded configuration, shown in FIG. 2, the distal electrode 114 and the proximal tine electrode are a first distance apart. In the second protruded configuration, shown in FIG. 3, the distal electrode 114 and the proximal electrode 126 are a second, larger distance apart as a result of the axial movement of the inner electrode assembly 102 with respect to outer electrode assembly 104.

When the ablation device 101 is being used in the human body for pulsed electric field ablation treatment, the distal portion 103 of the device is movable in the body independently of the proximal portion 105 of the device. Conversely, the proximal portion 105 is movable in the body independently of the distal portion 103. For example, the inner electrode assembly 102 may be held in static position in the body of a patient while the outer electrode assembly 104 is moved axially to shorten or lengthen the protrusion distance. Alternatively, the outer electrode assembly 104 may be held in a static position while the inner electrode assembly 102 is moved axially to shorten or lengthen the protrusion distance of the inner electrode assembly 102.

Additionally, the electrode arrays 124, 134 are retractable and expandable in the body independently of one another, and independently of movement of the proximal portion 105 and distal portion 103 of the ablation device 101.

The electrode arrays 124, 134 each have an expanded configuration, a partially expanded configuration, and an unexpanded configuration. In some examples, the expansion of the distal and proximal electrode arrays 124, 134 is continuously variable, meaning that the amount of protrusion of the tines 115, 127 can vary from completely retracted to completely expanded or any amount of expansion in between.

Figure 4A:
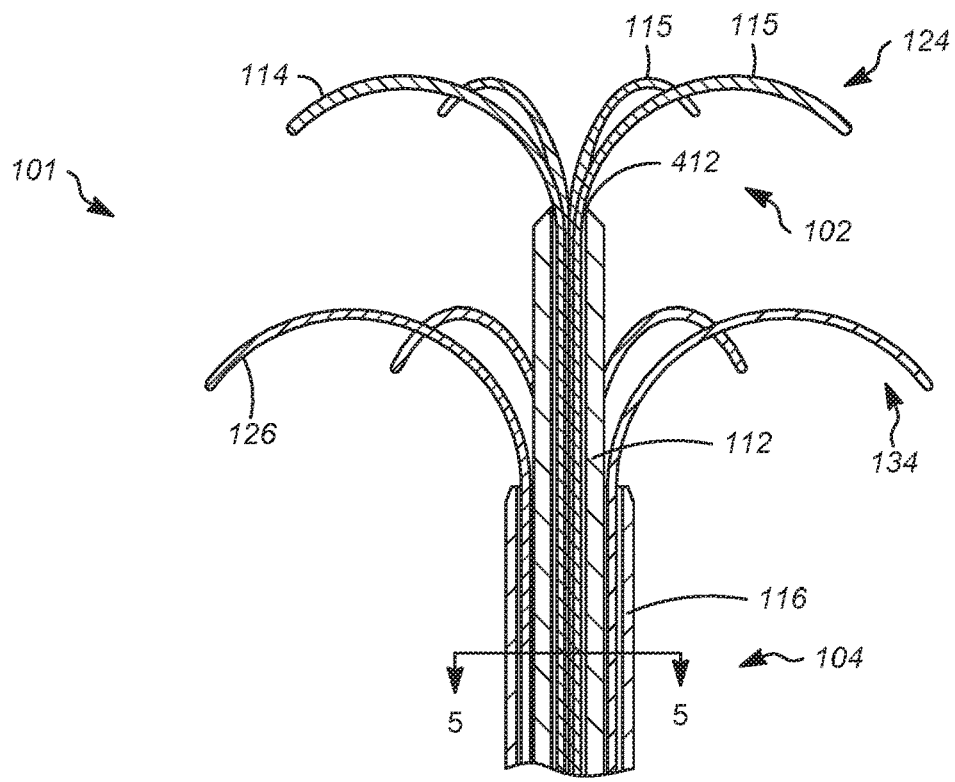
FIG. 4A is an axial cross-sectional view of an ablation probe according to some examples.
Figure 4B:
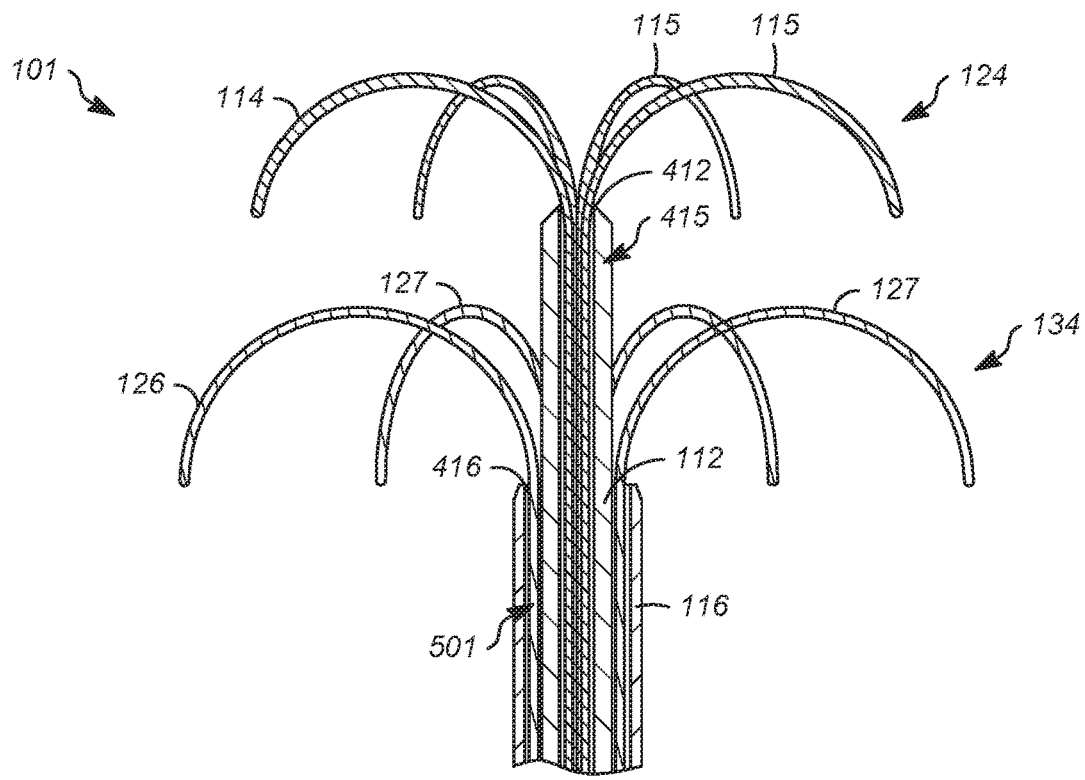
FIG. 4B is an axial cross-sectional of the ablation probe of FIG. 4A in a second configuration according to some examples.

FIGS. 4A-B show the proximal electrode array 134 and the distal electrode array 124 in a first expanded position and a second expanded position. In FIG. 4A, the plurality of tines 115 of the distal electrode array 124 protrude from the distal tip 412 of the inner elongate shaft 112 so that a particular tine length is protruding, and the plurality of tines 127 of the proximal electrode array 134 protrude from the distal tip 416 of the outer elongate shaft 116 by a particular tine length. In this first expanded position, the system can be used to deliver pulsed electric field energy to create an ablated lesion of a particular size and shape.

By further deploying the electrodes of the ablation device 101, the size and shape of the pulsed electric field, and therefore the size and shape of the ablation lesion can be changed. In FIG. 4B, the plurality of tines 115 of the distal electrode array 124 protrude from the distal tip 412 of the inner elongate shaft 112 by a greater tine length than in FIG. 4A, and the plurality of tines 127 of the proximal electrode array 134 protrude from the distal tip 416 of the outer elongate shaft 116 by a greater tine length than in FIG. 4A. In this second expanded position, the system can be used to deliver pulsed electric field energy to create a different lesion shape.

Both the distal electrode array 124 and the proximal electrode array 134 are also configured to have an unexpanded position (not shown) in which all of the electrode elements are retracted. When the inner electrode assembly 102 is in the unexpanded configuration, the plurality of electrode tines 115 are retracted into a lumen 415 of the inner elongate shaft 112. When the outer electrode assembly 104 is in the unexpanded configuration, the plurality of electrode tines 127 are retracted into the central passage 501 of the outer elongate shaft 116.

As mentioned, in some examples, the expansion of the distal and proximal electrode arrays 124, 134 is continuously variable, meaning that the amount of protrusion of each of the tines 115, 127 from the distal tip 412, 416, respectively, can vary from completely retracted to completely expanded or any amount of expansion or tine length in between.

It will be understood that the ablation device 101 can customize the size and shape of an ablation lesion both by adjusting the axial distance between the distal portion 103 and the proximal portion 105 of the ablation device 101, and by adjusting the expanded position of the expandable electrode arrays 124, 134. Additionally, the distal electrode array 124 is independently expandable and retractable of the proximal electrode array 134. For some examples, the distal electrode array 124 could be in a first expanded position while the proximal electrode array 134 is adjusted to be in the second expanded position. The opposite is also true: the proximal electrode array 134 could be in the first expanded position while the distal electrode array 124 is adjusted to be in the second expanded position.

Figure 5:
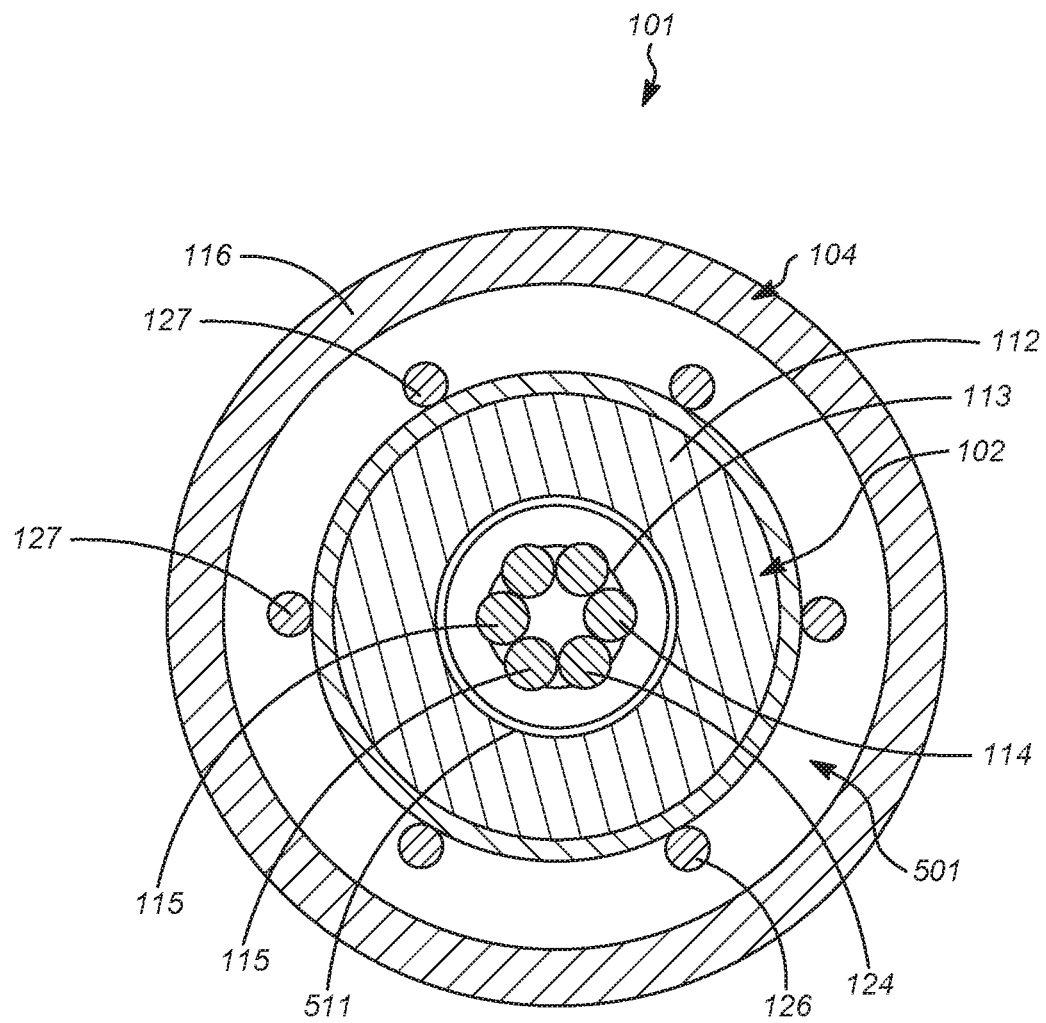
FIG. 5 is a radial cross-sectional view of the ablation probe of FIG. 4A along line 5-5 of FIG. 4A according to some examples.

FIG. 5 is a radial cross-sectional view of an ablation device of FIG. 4A along line 5-5 of FIG. 4A according to some examples. FIG. 5 shows the outer elongate shaft 116 and the inner elongate shaft 112. The outer elongate shaft defines a central passage 501. The central passage 501 is configured to slidably receive the inner electrode assembly 102. In some examples, the inner electrode assembly 102 is provided with an external layer 511 to electrically insulate the inner electrode assembly 102 from the outer electrode assembly 104. The inner electrode assembly 102 and the outer electrode assembly 104 each include a push rod structure which is connected to the electrode arrays. The pushrod 113 of the inner electrode assembly 102 is connected to the proximal end of the electrodes 114 of the distal electrode array 124. The push rod receives a linear force from the user and in response moves the electrode array axially within the shaft to protrude or retract from the distal end. Alternatively, a screw arm (not shown) could be provided with radial actuation of the electrodes. In that case, a rotational force of the screw would translate to expansion of the electrode assemblies 102 or 104. The pushrod of the outer electrode assembly 104 defines the central passage that receives the inner electrode assembly 102.

Figure 6:
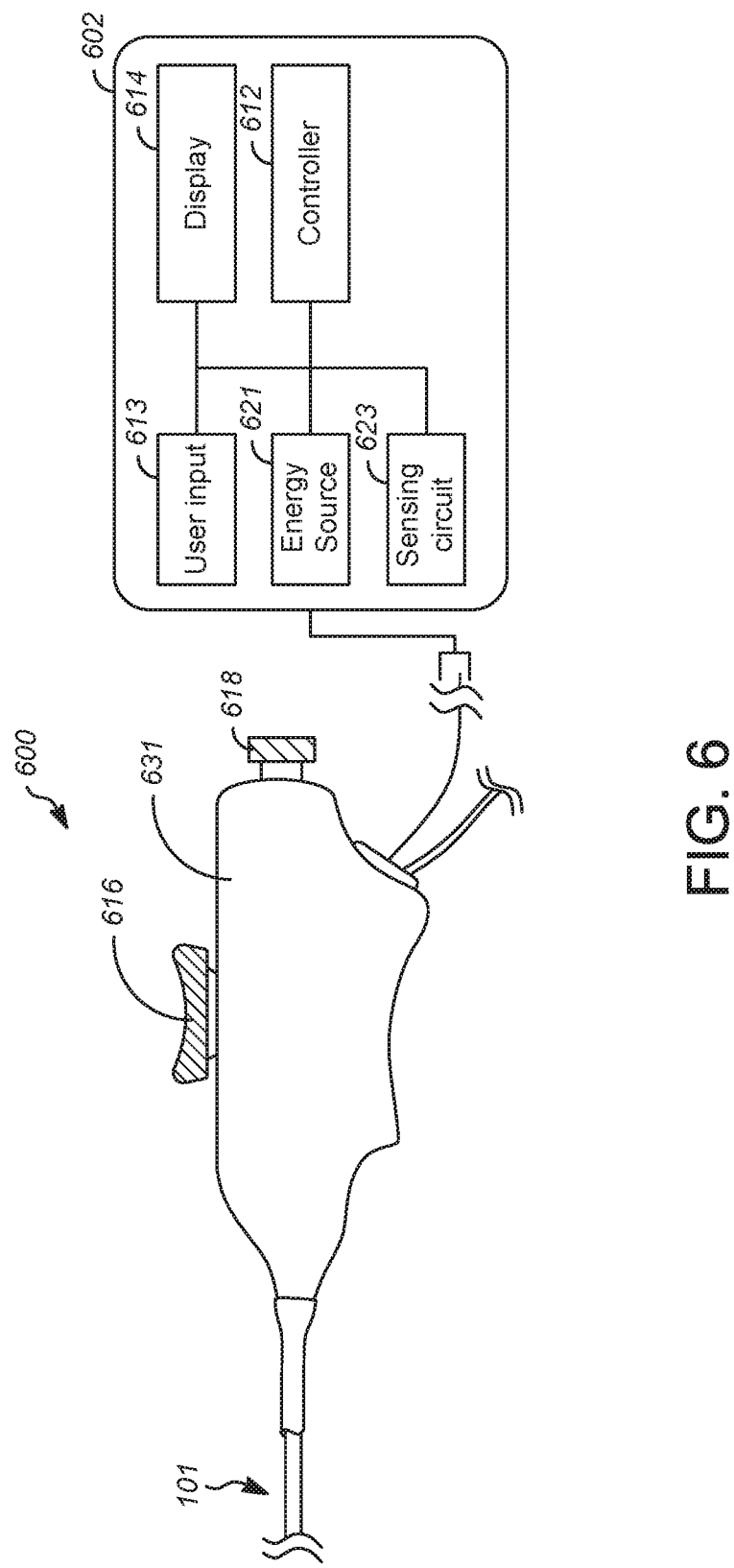
FIG. 6 is a schematic view of an ablation system according to some examples.

FIG. 6 is a schematic view of an ablation system according to some examples. The ablation system 600 includes an ablation control unit 602 that includes a controller 612. The control unit 602 includes a user input 613 and a display 614 to allow a user to interact with the controller 602. An energy source 621 is configured to provide pulsed electric field energy for reversible or irreversible electroporation of tissue. A sensing circuit 623 is provided. The sensing circuit 623 can be connected to the distal electrode 114, the proximal electrode 126, and other electrodes to generate a signal corresponding to the impedance of tissue between the two electrodes 114, 126. In addition or alternatively, the system can be configured to generate a signal corresponding to the impedance of tissue between one or more electrodes and a grounding pad. Impedance measurements can be used, for example, to create a three-dimensional model, a map, or a simulation to estimate ablation lesion volume and the effectiveness of the treatment. Known electrode geometry, spacing and deployment as well as PEF electrical settings can be inputs to the three-dimensional model, map, or simulation. Impedance sensing can be used to estimate lesion size, estimate treatment effectiveness, as an input to a recommendation or decision to end treatment, or any combination of these. Impedance sensing can provide evidence about lesion creation and tissue response that can be used during therapy or after therapy.

The ablation system includes the ablation device 101 and a handle 631 for manual manipulation of the ablation device 101. The ablation system is configured to deliver a pulsed electric field to the ablation device 101 for reversible or irreversible electroporation of tissue.

The handle 631 includes a port 618. The port 618 can be used to facilitate passage of devices through the central passage 501 of the outer elongate shaft 116, such as the inner electrode assembly 102 or a guidewire. The handle 631 includes an actuator 616 for deploying and retracting one or more of the electrode arrays. One or more additional actuators can be provided on the handle 631 for deploying and retracting other electrode arrays, controlling the axial movement of one or more electrode assemblies, or both. In addition or alternatively, the axial movement of one or more of the electrode assemblies and electrode arrays is controlled with a motorized sled to automatically deploy or retract or move axially.

Figure 7:
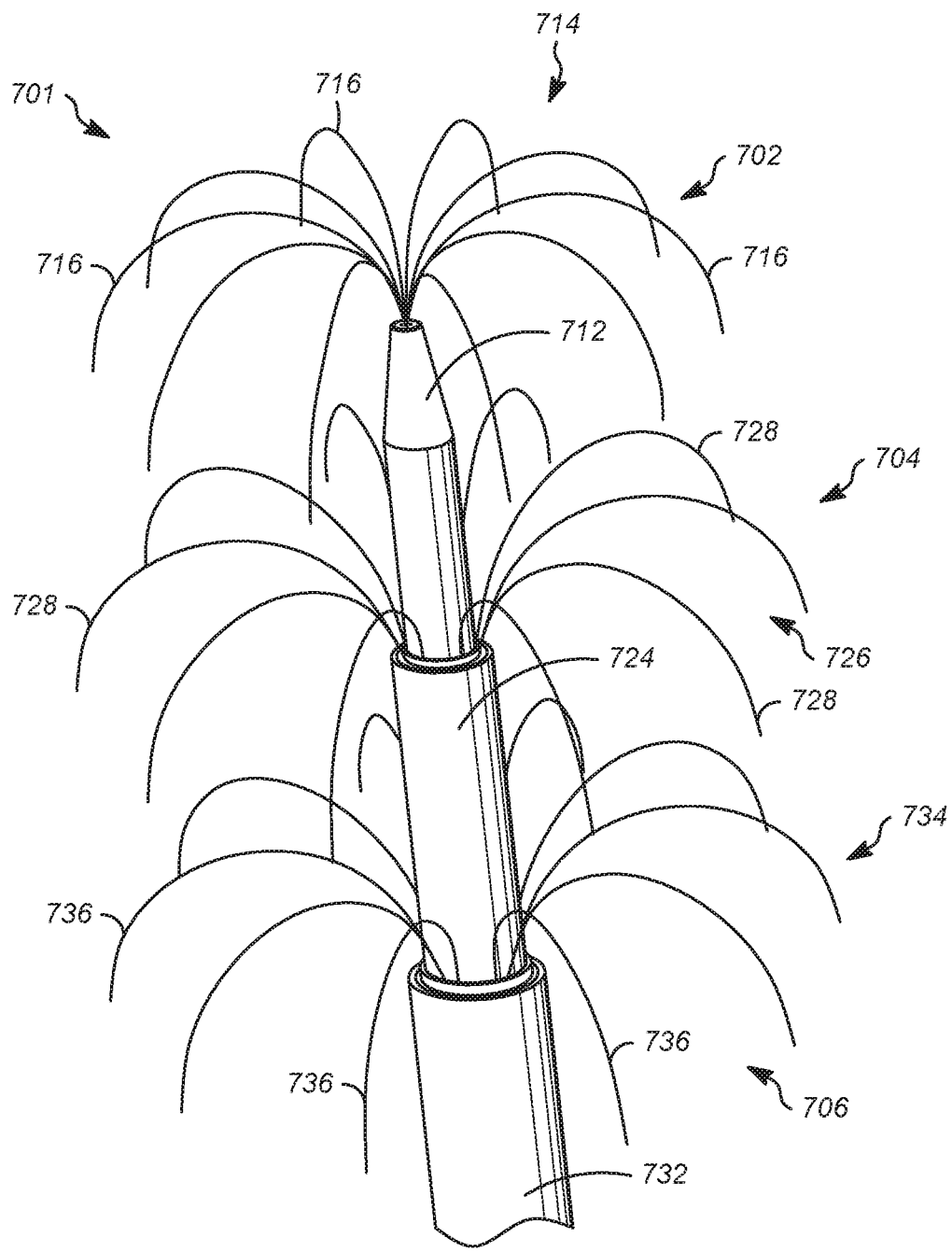
FIG. 7 is a perspective view of an alternative ablation probe according to some examples.

FIG. 7 is a perspective view of an alternative ablation device according to some examples. The ablation device 701 has a distal electrode assembly 702, a proximal electrode assembly 706, and an intermediate electrode assembly 704 that is situated between the distal and proximal electrode assemblies 702, 706. The distal electrode assembly 702 can be similar to the electrode assembly 102 of FIG. 1, and the proximal electrode assembly 706 can be similar to the outer electrode assembly 104 of FIG. 1. The distal electrode assembly 702 includes a distal shaft 712 and a distal electrode array 714, which includes a plurality of electrode elements 716. The intermediate electrode assembly 704 includes an intermediate shaft 724 and an expandable electrode array 726, which includes a plurality of electrode elements 728. The proximal electrode assembly 706 includes a proximal shaft 732, and an electrode array 734, which includes a plurality of electrode elements 736. The proximal shaft 732 has a central passage configured to slidably receive the intermediate shaft 724. In turn, the intermediate shaft 724 defines a central passage configured to slidably receive the distal shaft 712.

The three electrode assemblies 702, 704, 706 move in a telescoping manner to modify the axial distance between the electrode assemblies. The electrode assemblies 702, 704, 705 can also be referred to as electrode delivery assemblies. The intermediate electrode assembly 704 is independently axially movable with respect to both the distal electrode assembly 702 and the proximal electrode assembly 706. Similarly, the distal electrode assembly 702 is independently axially movable with respect to the intermediate electrode assembly 704 and the proximal electrode assembly 706. The electrode arrays 714, 726, and 734 each have expanded, partially expanded, and unexpanded positions, similar to the electrode arrays 124 and 134 of FIG. 1. In some examples, the expansion of the electrode arrays 714, 726, and 734 is continuously variable, meaning that the amount of protrusion of the tines can vary from completely retracted to completely expanded or any amount of expansion in between.

Figure 8:
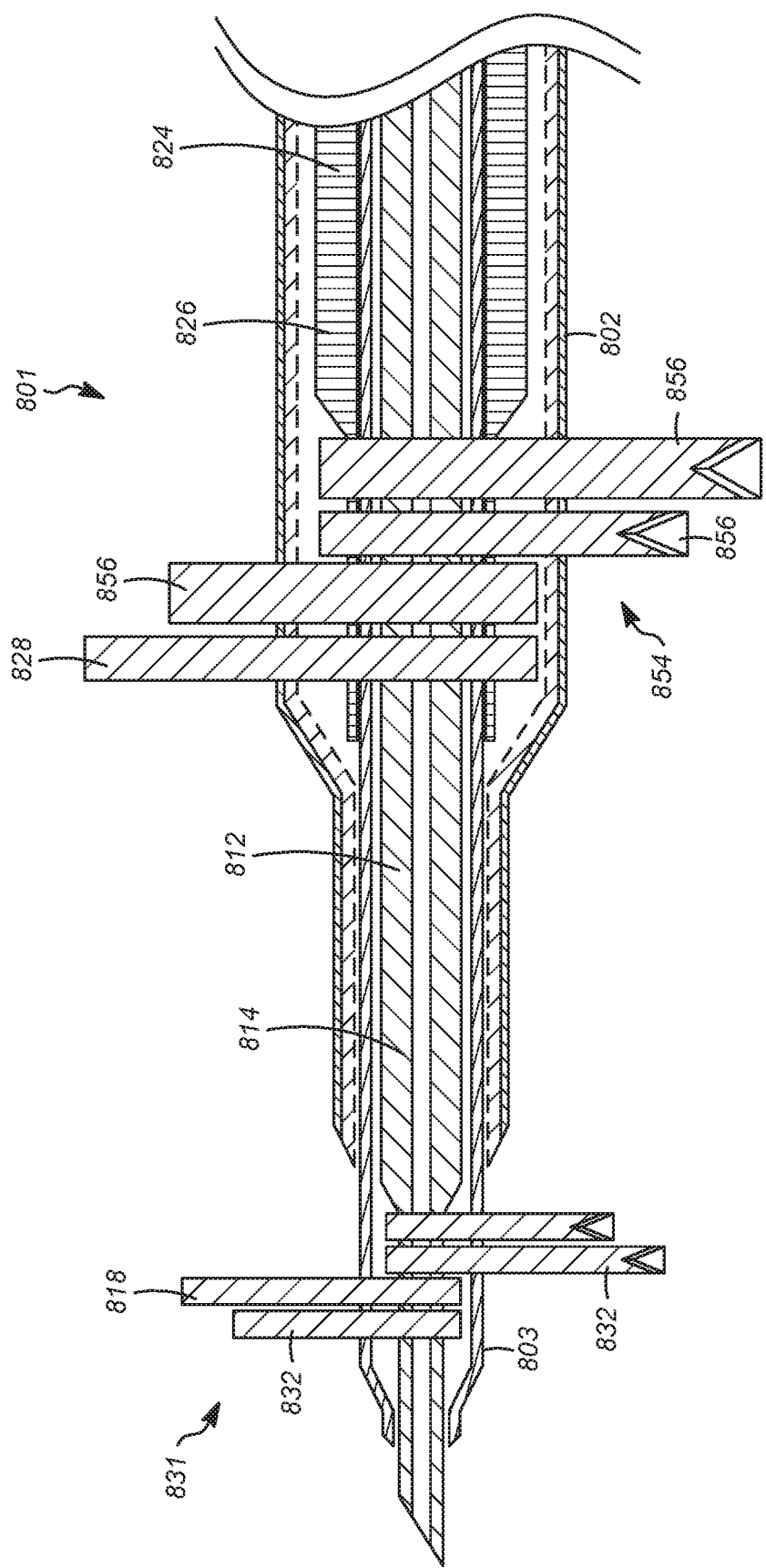
FIG. 8 is a cross-sectional view of an alternative ablation probe according to some examples.

Electrode Arrays that Expand via Rotation (FIG. 8)

FIG. 8 is a cross-sectional view of an alternative ablation device according to some examples. The ablation device 801 includes an inner electrode assembly 812 comprising an inner elongate shaft 814 and a distal electrode 818. The ablation device 801 further includes an outer electrode assembly 824 with an outer elongate shaft 826 and a proximal electrode 828. Both the inner electrode assembly 812 and the outer electrode assembly 824 are contained within a sheath 802. The outer electrode assembly 824 defines a central passage configured to slidably receive the inner electrode assembly 812. The inner electrode assembly 812 and the outer electrode assembly 824 are axially movable with respect to one another.

In some examples, the inner electrode assembly 812 includes an expandable distal electrode array 831 that is expandable between an unexpanded position and an expanded position. The distal electrode array 831 includes a plurality of electrode elements 832. The plurality of electrode elements 832 can include the distal electrode 818. In an unexpanded configuration (not shown), the electrode elements 832 are retracted inside of the sheath 803. In the unexpanded configuration, the electrode elements 832 wrap around the circumference of the inner elongate shaft 814. The distal electrode array 831 can be deployed by holding the outer elongate shaft 826 stationary while rotating the inner elongate shaft 814 clockwise. The distal electrode array 831 can be retracted by holding the outer elongate shaft 826 stationary and rotating the inner elongate shaft 814 counterclockwise. In some examples, the expansion of the distal electrode array 831 is continuously variable, in that the electrode elements 832 can be completely retracted, completely expanded, or partially expanded in any amount between full expansion and full retraction.

In some examples, the outer electrode assembly 826 includes an expandable proximal electrode array 854 that is expandable between an unexpanded position and an expanded position. The proximal electrode array 854 includes a plurality of electrode elements 856. The plurality of electrode elements 856 can include the proximal electrode 828. In an unexpanded configuration (not shown), the electrode elements 856 are retracted inside of the sheath 802. In the unexpanded configuration, the electrode elements 856 wrap around the circumference of the outer elongate shaft 826. The proximal electrode array 854 can be deployed by holding the sheath 802 stationary while rotating the outer elongate shaft 826 clockwise. The proximal electrode array 854 can be retracted by holding the sheath 802 stationary while rotating the outer elongate shaft 826 counterclockwise. In some examples, the expansion of the proximal electrode array 854 is continuously variable, in that the electrode elements 856 can be completely retracted, completely expanded, or partially expanded in any amount between full expansion and full retraction.

The inner electrode assembly 812 and the outer electrode assembly 824 are axially movable with respect to one another. The inner elongate shaft 814 is independently movable of the outer elongate shaft 826. Thus, the distance between the distal electrode array 831 and the proximal electrode array 854 is adjustable to create a desired lesion shape during a pulsed electric field ablation treatment.

It will be understood that the ablation device 801 can customize the size and shape of an ablation lesion both by adjusting the axial position of the inner electrode assembly 812 and the outer electrode assembly 824, and by adjusting the expanded position of the expandable electrode arrays 831, 854. Additionally, the distal electrode array 831 is independently expandable and retractable of the proximal electrode array 854. That is, in some examples, the distal electrode array 831 could be in a first expanded position while the proximal electrode array 854 is adjusted to be in a different expanded position.

Electrode Arrays that Expand via Inflation or a Linear Force (FIGS. 9-14)

Figure 9:
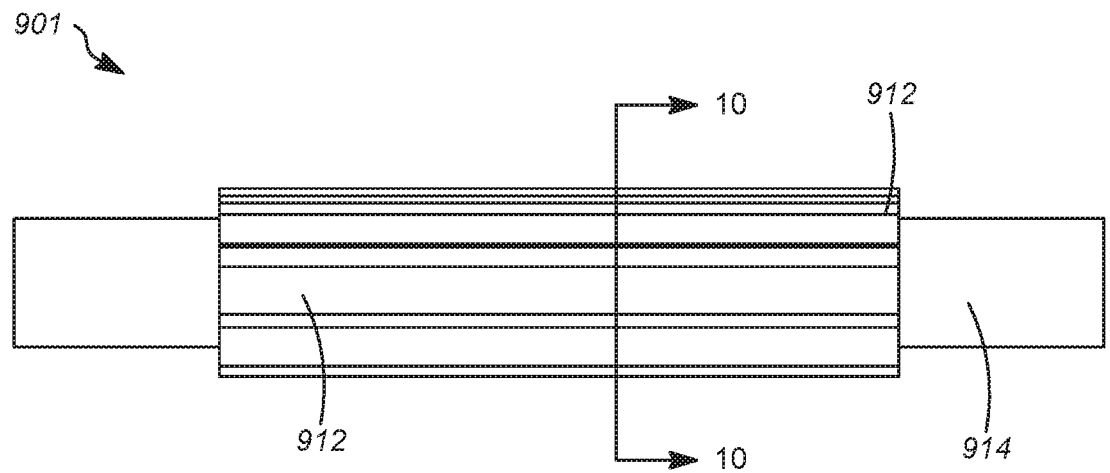
FIG. 9 is a side view of an ablation device in an unexpanded state according to some examples.
Figure 10:
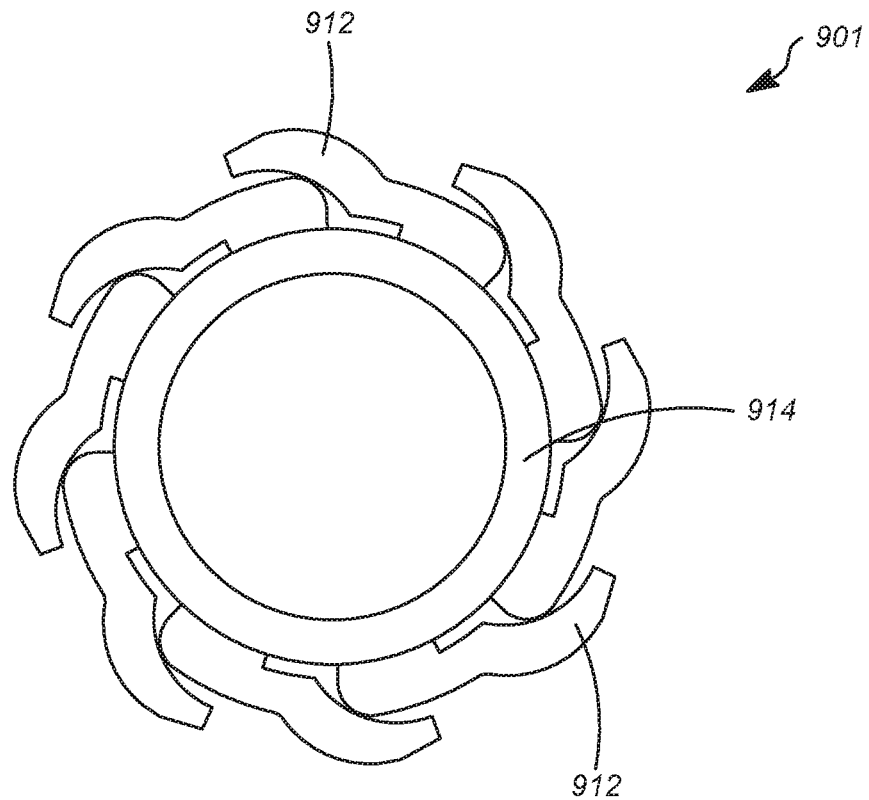
FIG. 10 is cross-sectional view of the ablation device of FIG. 9 in the unexpanded state along line 10-10 according to some examples.
Figure 11:
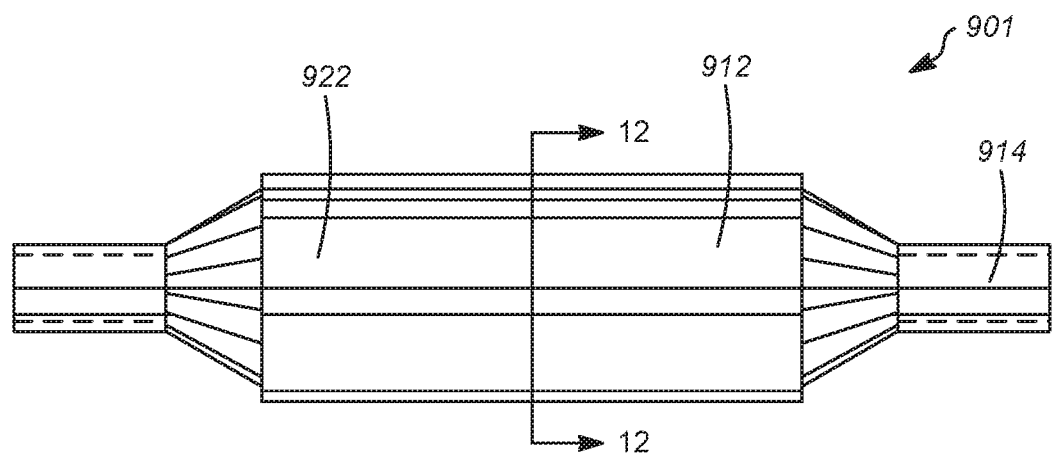
FIG. 11 is a side view of the ablation device of FIG. 9 in an expanded state according to some examples.
Figure 12:
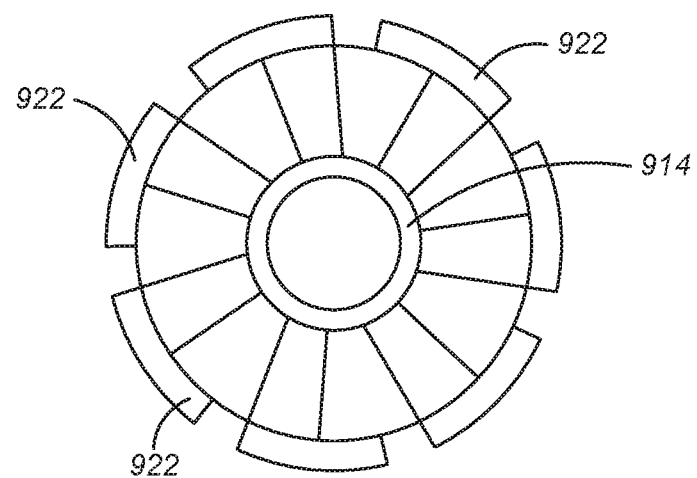
FIG. 12 is a cross-sectional view of the ablation device of FIG. 9 in the expanded state along line 12-12 according to some examples.

FIGS. 9-12 show an alternative example of an expandable electrode array. The expandable electrode array 901 is a balloon-type expandable member, a pull-wire type expandable member, or a push-wire expandable member. The electrode array 901 can be used as an alternative to the expandable electrode arrays 124, 134. FIGS. 9 and 10 show the electrode array 901 in an unexpanded position. FIG. 10 is a cross-sectional view of FIG. 9 along line 10-10. and FIGS. 11-12 show the electrode array 901 in an expanded position. FIG. 12 is a cross-sectional view of FIG. 11 along line 12-12.

The electrode array 901 has a plurality of collapsible members 912 situated around a central core 914. When provided around a balloon-type expandable member, the electrode array 901 goes from an unexpanded position to an expanded position by a radially-acting mechanism provided by inflation of the balloon that is surrounded by the collapsible member 912. When provided around a pull-wire type expandable member, the electrode array 901 goes from an unexpanded position to an expanded position by a linear force provided by a pull wire pulling axially in a proximal direction on the distal end of the expandable electrode array 901. The electrode array 901 goes from an expanded position to an unexpanded position by a linear force provided by a pull wire pushing axially in a distal direction on the distal end of the expandable electrode array 901. The collapsible members 912 can be made of a shape-memory material. The electrode array 901 includes a plurality of electrodes 922 that can be used in connection with the system of FIG. 6 to perform pulsed electric field ablation, including reversible and irreversible electroporation of tissue.

Figure 13:
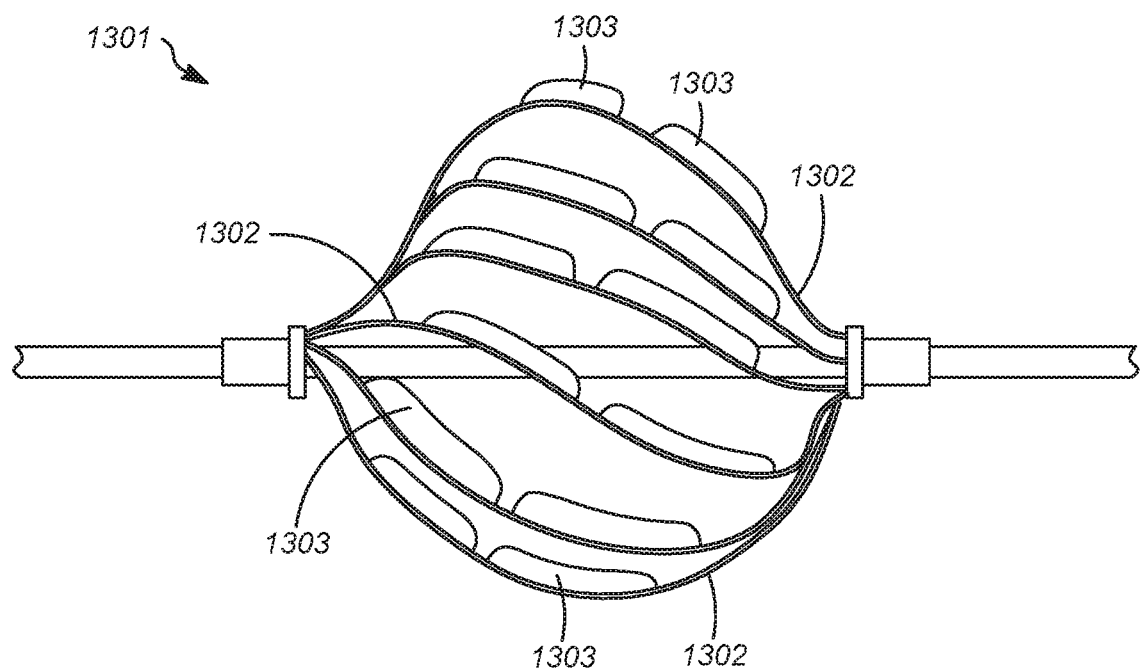
FIG. 13 is a side view of an ablation device according to some examples.
Figure 14:
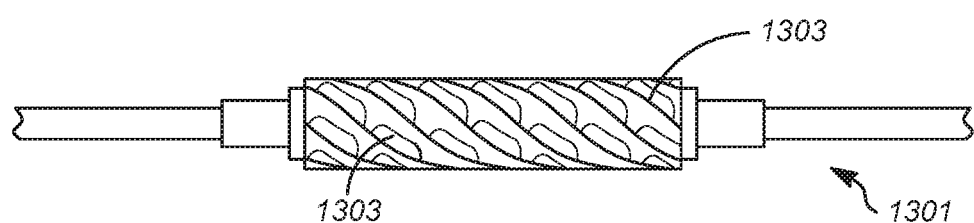
FIG. 14 is a side view of the ablation device of FIG. 13 according to some examples.
Figure 15:
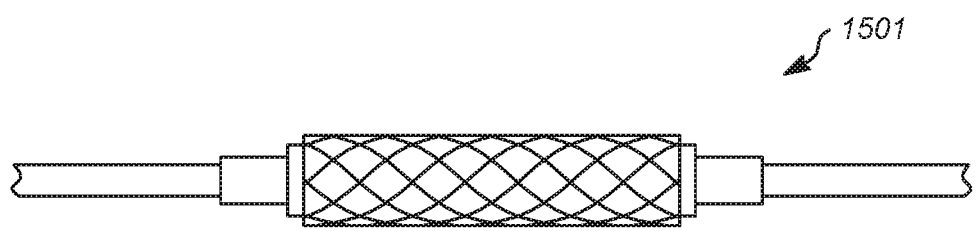
FIG. 15 is a side view of an alternative ablation device according to some examples.

FIGS. 13-15 show alternative examples of expandable electrode arrays, which can be used as alternatives to the expandable electrode arrays 124, 134. FIG. 13 shows the electrode array 1301 in an expanded position and FIG. 14 shows the electrode array 1301 in an unexpanded position.

The electrode array 1301 includes a plurality of collapsible members 1302 that carry a plurality of electrodes 1303. The collapsible members 1302 can be moved from an unexpanded position to an expanded position by a linear force provided by a pull wire, pull tube, or other pull mechanism pulling axially in a proximal direction on the distal end of the expandable electrode array 1301. The collapsible members 1302 can be moved from an expanded position to an unexpanded position by a linear force provided by the pull mechanism pushing axially in a distal direction on the distal end of the expandable electrode array 1301. Alternatively or in addition, a pull mechanism can act on the proximal end of the expandable electrode array 1301 to move it between the expanded and unexpanded states.

The collapsible members 1302 can be made of a shape-memory material. In some embodiments, the collapsible members 1302 have a resting state in the unexpanded position, and are moved into the expanded position using a pull mechanism. In some embodiments, the collapsible members 1302 have a resting state in the expanded position, are held in the unexpanded position using the pull mechanism, and can be released into the expanded position. In one embodiment, the collapsible members 1302 are configured to be spiral-wrapped in one direction to provide a fully expanded configuration. In addition or alternatively, the pull mechanism can be a tube attached to the proximal end of the expandable electrode array, and can be twisted by the user to modify the shape and wrap configuration of the collapsible member 1302.

The diameter of the expandable electrode array 1301 in the expanded position is adjustable by the user according to the application needs and depending on how much the user actuates a pull mechanism and whether the user applies torque to the pull mechanism, in some examples. In addition or alternatively, the collapsible members 1302 can be moved from an unexpanded position to an expanded position using a balloon member within the collapsible members 1302.

FIG. 15 shows an electrode array 1501 in an unexpanded position in an alternative example. In this example, the electrode array 1501 includes a wire mesh or wire braid arrangement, such as using a shape-memory material, for example Nitinol. The actuation mechanisms discussed above with respect to FIGS. 13-14 also apply to the electrode array 1501 to move electrode array 1501 between the unexpanded configuration shown in FIG. 15 and an expanded configuration. The electrodes of the electrode array 1501 can be located or connected at the intersections of wire material or at the straight sections of the wire material in between intersections.

Control of Axial Movement of Electrode Assemblies

Electrode assemblies, such as the inner electrode assembly, the intermediate electrode assembly, or the outer electrode assembly, can be inserted, retracted, and moved within a channel of another electrode assembly by a number of different methods. Control can be manual, for example when an electrode assembly is inserted by hand into a port. In this situation, the electrode assembly can have multiple insertion depth markings on the shaft of the electrode assembly. The markings can be evenly spaced and labeled to indicate the insertion depth of the electrode assembly. Alternatively, or in addition, the system can provide a locking mechanism that holds one electrode assembly in place with respect to another electrode assembly or to the ablation system. Alternatively, or in addition, the electrode assembly can be provided with mechanical means to move the device within a central channel of another electrode assembly, such as the outer electrode assembly or intermediate electrode assembly. Examples of mechanical means to move the device include a screw assembly that translates rotational motion of a screw to linear axial motion of the electrode assembly. Alternatively, or in addition, insertion and retraction of the electrode assembly can be controlled electronically using a motored assembly.

Mechanical Spacing of Electrode Structures

In some embodiments, mechanical structures are used to cause a desired electrode spacing, configuration, or both in order to obtain the desired electric field. In some embodiments, the electrode elements include masked portions where the conductive material of the electrode element is insulated in order to change the electric field. In other embodiments, an outer cannula is provided that shields the tissue from portions of the electrode elements to change the electric field. In some examples, the electrode spacing can be precisely adjusted or manipulated through various mechanisms to control electrode size and spacing, thus controlling subsequent ablation volume and three-dimensional simulations.

Shaft of Elongate Electrode Assembly

Each electrode assembly having an electrode or an electrode array includes a structure for providing an electrical connecting to the electrode or electrode array. In some examples, that structure is also used to deploy an expandable electrode array. In some examples, that structure defines a central passage for accommodating an inner electrode assembly, an intermediate electrode assembly, or both. In some examples, that structure is the elongate shaft of the electrode assembly. The elongate shaft can be a tube made of a suitable material. In some examples, the shaft of the elongate electrode assembly includes a coiled material or micromachined material. Suitable materials include stainless steel or a polymer. In some examples, an insulating lining can be provided on the inner diameter of the shaft. The shaft can be provided with a compression tensile sufficient to deploy and retract an electrode array within the ablation catheter in response to a linear force on the proximal end of the shaft. In some examples, the shaft has a wall thickness of at least 0.003 inches. In some examples, the shaft has a wall thickness of 0.015 inches or less. In some examples, the wall thickness is between about 0.003 inches and about 0.015 inches, inclusive of those values.

In some examples, the tube has an inner diameter of at least 2 French (0.66 mm). In some examples, the tube has an outer diameter of 10 French (3.33 mm) or less. In some examples, the tube has an inner diameter of between 2 French and 10 French, inclusive of those values.

In some examples, the shaft has an outer diameter of at least 0.025 inches. In some examples, the shaft has an outer diameter of 0.158 inches or less. In some examples, the shaft has an outer diameter of between about 0.025 inches and about 0.158 inches, inclusive of those values.

In some examples, the shaft has a length of at least 10 cm. In some examples, the shaft has a length of 40 cm or less. In some examples, the shaft has a length of between about 10 cm and about 40 cm. In one example, the tube is an SAE type 304 stainless steel tube with an inner diameter of 0.027 inch (0.69 mm), an outer diameter of 0.039 inch (0.99 mm), and a wall thickness of 0.006 inch (0.15 mm).

Leads

The electrode assemblies of the various examples of the technology are provided with electrically conductive leads to convey energy from a generator outside of the ablation catheter to the electrodes inside of a patient's body. The leads are configured to electrically connect the electrode elements of the electrode assembly to an external generator.

The leads can be situated in a number of different configurations, based on the particular implementation of the ablation catheter. For example, a shaft of the electrode assembly itself can be constructed from an electrically conductive material, such as stainless steel, in which case the shaft can serve as the lead. In alternative examples, a wire positioned on the inner surface or the outer surface of the electrode assembly shaft can be used as a lead. In alternative examples, a lead can be placed within a wall of the electrode assembly, or the lead can be a conductive trace on the inner surface or the outer surface of the electrode assembly.

Each electrode assembly is provided with at least one lead. A separate lead can be provided for each electrode of an electrode assembly, so that individual electrodes can be held at different potentials.

Electrode Elements and Electrode Arrays

While particular exemplary embodiments of electrode elements and electrode arrays, are provided, the disclosure is not limited to the specific examples herein. Additional configurations are contemplated. In some examples, the electrode arrays are expandable from a first retracted position inside of the ablation catheter to an expanded position outside of the ablation catheter. In some examples, an electrode assembly includes a single electrode. In some examples, an electrode array comprises two or more electrode elements positioned at the distal portion of the electrode assembly. In some examples, an electrode array or electrode assembly comprises three or more electrode elements positioned at the distal portion of the electrode assembly. In some examples, an electrode array or electrode assembly comprises four or more, five or more, six or more, or seven or more electrode elements positioned at the distal portion of the electrode assembly. The electrode array can be configured so that when the electrode elements are expanded and deployed, the electrode elements surround the exterior of the ablation catheter circumferentially, although this is not necessary. In some examples, the electrode elements can be deployed selectively such that some electrode elements are in a retracted position at the same time that other electrode elements are in an expanded position. In some examples, multiple electrode elements are present and the distance between the electrode elements is adjustable.

In some examples, the expansion of an electrode array is continuously variable, meaning that the amount of protrusion of electrode elements can vary from completely retracted to completely expanded or any amount of expansion in between.

In some examples, the electrode elements can be electrically conductive tines, such as a conductive shape memory alloy material such as nickel titanium alloy (nitinol). In alternative examples, the electrode elements can be a conductive metal like stainless steel, gold, copper, silver, or platinum. In some examples, the electrode elements can include a polymer coating layer with a paste, gel, or ribbon that has conductive properties. Alternatively, plating or coatings can be used as conductive materials on either the tines or shaft electrodes.

The electrode elements of the various examples can be attached to the electrode assembly using a number of different constructions. For example, if the electrode assembly shaft is metal and the electrode elements are metal, the two can be welded together. In alternative arrangements, the electrode elements can be integrally constructed from the electrode assembly material, such as one when the electrode assembly shaft is a metal tube. In this example, the tube can be cut to the correct proportions to create the electrode elements. In alternative examples, the electrode elements can be attached using a collar or could be looped through openings at the end of the shaft.

Parameters for Irreversible Electroporation

For irreversible electroporation, the pulse width ranges from about 10 nanoseconds to about 1 microsecond, or about 0.5 microseconds to 100 microseconds, or about 1 microsecond to 75 microseconds. The pulse can be either monophasic or biphasic (has both positive and negative). The voltage ranges from 200 Volts to 5000 Volts, preferably 1000 Volts to 3000 Volts, to have the electrical field strength in tissue from 500 Volts per centimeter (V/cm) to 2500 V/cm, preferably 1000 V/cm to 2500 V/cm to cause cell damage.

Ablation Methods

The various examples of ablation devices provided in the present disclosure can be used to perform an ablation method. The method can be used with an ablation probe that has an inner electrode assembly with an inner elongate shaft and a distal electrode and an outer electrode assembly with an outer elongate shaft and a proximal electrode. Either the inner electrode assembly or the outer electrode assembly includes an expandable electrode array. The method of ablation includes inserting the ablation probe into tissue of the patient and moving the electrode array from an unexpanded position into an expanded position. The method proceeds by delivering a pulsed electric field energy to both the distal electrode and the proximal electrode. The method includes moving the distal electrode and the proximal electrode axially with respect to one another.

In some examples, the pulsed electric field is delivered at the same time that the distal electrode and the proximal electrode are being moved axially from one another. In some examples, the expandable electrode array is a distal electrode array containing the distal electrode, and the pulsed electric field ablation treatment occurs while moving the proximal electrode axially with respect to the distal electrode.

In some examples, the method further includes delivering a second pulsed electric field after moving the distal electrode and the proximal electrode axially with respect to one another. In some examples, a second pulsed electric field is delivered after moving the proximal electrode axially with respect to the distal electrode while the proximal electrode is held stationary. In some examples, a second pulsed electric field is delivered while performing at least one of: moving the first electrode array from the expanded position to the unexpanded position, moving the first electrode array axially, and moving the first electrode array from the unexpanded position to the expanded position. In some examples, a second pulsed electric field is delivered while moving the first electrode array from a first expanded position to a second, further expanded position. In some examples, the method further includes providing an individual electric polarity to the distal electrode, the proximal electrode, and each of the elements in the expandable electrode array.

As used in this specification and the appended claims, the singular forms include the plural unless the context clearly dictates otherwise. The term "or" is generally employed in the sense of "and/or" unless the content clearly dictates otherwise. The phrase "configured" describes a system, apparatus, or other structure that is constructed or configured to perform a particular task or adopt a particular configuration. The term "configured" can be used interchangeably with other similar terms such as arranged, constructed, manufactured, and the like.

All publications and patent applications referenced in this specification are herein incorporated by reference for all purposes.

While examples of the technology described herein are susceptible to various modifications and alternative forms, specifics thereof have been shown by way of example and drawings. It should be understood, however, that the scope herein is not limited to the particular examples described. On the contrary, the intention is to cover modifications, equivalents, and alternatives falling within the spirit and scope herein.

What is claimed is:

1. A system for ablation, comprising:
an inner electrode assembly comprising an inner elongate shaft and a first expandable electrode array;
an outer electrode assembly comprising an outer elongate shaft and a second expandable electrode array;
wherein the inner electrode assembly and the outer electrode assembly are contained within a sheath;
wherein the outer electrode assembly defines a central passage configured to slidably receive the inner electrode assembly, wherein the first expandable electrode array or the second expandable electrode array is axially moveable with respect to the other; and
an energy source configured to be electrically connected to the first expandable electrode array and the second expandable electrode array and configured to deliver a pulsed electric field (PEF);
wherein each of the first expandable electrode array and the second expandable electrode array comprise two or more electrode elements moveable between an unexpanded position and an expanded position, wherein the two or more electrode elements of the first expandable electrode array are configured to wrap around a circumference of the inner elongate shaft when in the unexpanded position, further wherein the two or more electrode elements of the second expandable electrode array are configured to wrap around a circumference of the outer elongate shaft when in the unexpanded position;
wherein the inner electrode assembly is configured to be deployable by holding the outer elongate shaft stationary while rotating the inner elongate shaft in a first direction so that the two or more electrode elements of the first expandable electrode array are drawn out of the sheath;
wherein the inner electrode assembly is configured to be retractable into the sheath by holding the outer elongate shaft stationary while rotating the inner elongate shaft in a second direction opposite to the first direction so that the two or more electrode elements of the first expandable electrode array wrap around the circumference of the inner elongate shaft;
wherein the outer electrode assembly is configured to be deployable by holding the sheath stationary while rotating the outer elongate shaft in a third direction so that the two or more electrode elements of the second expandable electrode array are drawn out of the sheath;
wherein the outer electrode assembly is configured to be retractable into the sheath by holding the sheath stationary while rotating the outer elongate shaft in a fourth direction opposite to the third direction so that the two or more electrode elements of the second expandable electrode array wrap around the circumference of the outer elongate shaft;
wherein the two or more electrode elements of each of the first expandable electrode array and the second expandable electrode array are retractable into the sheath and deployable out of the sheath independently of an axial movement of each of the first expandable electrode array and the second expandable electrode array.

2. The system of claim 1, wherein the expanded position of the first expandable electrode array includes at least a first expanded position and a second, further expanded position, wherein the system is configured to deliver the PEF in the first expanded position and in the second expanded position.

3. The system of claim 1, wherein the system is configured to provide each of the two or more electrode elements of the first expandable electrode array and each of the two or more electrode elements of the second expandable electrode array with an individually controlled electric polarity.

4. The system of claim 1, further comprising an intermediate electrode assembly comprising an intermediate elongate shaft and an intermediate electrode, the intermediate elongate shaft defining a central passage configured to slidably receive the inner electrode assembly, wherein the intermediate elongate shaft is configured to be received within the central passage of outer electrode assembly.

5. The system of claim 4, wherein the intermediate electrode is part of the first expandable electrode array.

6. The system of claim 1, wherein the first expandable electrode array is an elongate electrode array configured to contact an elongated portion of a vessel wall.

7. The system of claim 1, further comprising a handle assembly operably connected to the inner electrode assembly and the outer electrode assembly.

8. The system of claim 7, wherein the handle assembly comprises a port configured to facilitate passage of a device through the central passage of the outer electrode assembly.

9. The system of claim 1, wherein the two or more electrode elements of the first expandable electrode array are welded to the inner elongate shaft, further wherein the two or more electrode elements of the second expandable electrode array are welded to the outer elongate shaft.

10. The system of claim 1, further comprising a sensing circuit connected to the two or more electrode elements of the first expandable electrode array and the two or more electrode elements of the second expandable electrode array, wherein the sensing circuit is configured to generate at least one signal corresponding to an impedance measurement of a tissue.

11. The system of claim 10, wherein the impedance measurement of the tissue is configured to generate a three-dimensional model of an ablation lesion.

12. An ablation method, comprising:
providing an ablation probe, comprising:
an inner electrode assembly comprising an inner elongate shaft and a first expandable electrode array; and
an outer electrode assembly comprising an outer elongate shaft and a second expandable electrode array, wherein the outer electrode assembly defines a central passage configured to slidably receive the inner electrode assembly, and wherein the first expandable electrode array or the second expandable electrode array is axially moveable with respect to the other;
wherein the inner electrode assembly and the outer electrode assembly are contained within a sheath;
wherein each of the first expandable electrode array and the second expandable electrode array comprises two or more electrode elements;
moving each of the first expandable electrode array and the second expandable electrode array from an unexpanded position to an expanded position, wherein the inner electrode assembly is configured to be deployable by holding the outer elongate shaft stationary while rotating the inner elongate shaft in a first direction so that the two or more electrode elements of the first expandable electrode array are drawn out of the sheath, wherein the inner electrode assembly is configured to be retractable into the sheath by holding the outer elongate shaft stationary while rotating the inner elongate shaft in a second direction opposite to the first direction so that the two or more electrode elements of the first expandable electrode array wrap around a circumference of the inner elongate shaft, wherein the outer electrode assembly is configured to be deployable by holding the sheath stationary while rotating the outer elongate shaft in a third direction so that the two or more electrode elements of the second expandable electrode array are drawn out of the sheath, and wherein the outer electrode assembly is configured to be retractable into the sheath by holding the sheath stationary while rotating the outer elongate shaft in a fourth direction opposite to the third direction so that the two or more electrode elements of the second expandable electrode array wrap around a circumference of the outer elongate shaft; and delivering a pulsed electric field (PEF) to the two or more electrode elements on the first expandable electrode array or the second expandable electrode array;

wherein the two or more electrode elements of the first expandable electrode array are configured to wrap around the circumference of the inner elongate shaft when in the unexpanded position, further wherein the two or more electrode elements of the second expandable electrode array are configured to wrap around the circumference of the outer elongate shaft when in the unexpanded position; and wherein the two or more electrode elements of each of the first expandable electrode array and the second expandable electrode array are retractable into the sheath and deployable out of the sheath independently of an axial movement of each of the first expandable electrode array and the second expandable electrode array.

13. The method of claim 12, wherein delivering the PEF occurs while moving one of the two or more electrode elements of the first expandable array and one of the two or more electrode elements of the second expandable array axially with respect to the other.

14. The method of claim 12, wherein delivering the PEF occurs while moving one of the two or more electrode elements of the second expandable array axially with respect to the two or more electrode elements of the first expandable electrode array.

15. The method of claim 12, further comprising delivering a second PEF after performing at least one of the following steps:

moving the two or more electrode elements of the second expandable array axially with respect to the two or more electrode elements of the first expandable array while the two or more electrode elements of the second expandable array are held stationary; and wherein the expanded position comprises a first expanded position and a second further expanded position, and moving the first expandable electrode array from the first expanded position to the second further expanded position.

16. The method of claim 12, further comprising providing each of the two or more electrode elements of the second expandable array and each of the two or more electrode elements of the first expandable electrode array an individually controlled electric polarity.

17. The method of claim 12, wherein the ablation probe further comprises a sensing circuit connected to the two or more electrode elements of the first expandable electrode array and the second expandable electrode array, wherein the sensing circuit is configured to generate at least one signal corresponding to an impedance measurement of a tissue.

18. The method of claim 17, further comprising estimating an effectiveness of the pulsed electric field based on the impedance measurement of the tissue.

19. The method of claim 12, wherein the two or more electrode elements of the first expandable electrode array are welded to the inner elongate shaft.

* * * * *